(12) United States Patent
Cheung et al.

(10) Patent No.: US 6,979,542 B2
(45) Date of Patent: Dec. 27, 2005

(54) METHODS FOR IDENTIFYING HETEROZYGOUS CARRIERS OF AUTOSOMAL RECESSIVE DISEASES

(75) Inventors: Vivian G. Cheung, Narberth, PA (US); Richard S. Spielman, Narberth, PA (US)

(73) Assignees: The Children's Hospital of Philadelphia, Philadelphia, PA (US); The Trustees of the University of Pennsylvania, Philadelphia, PA (US)

( * ) Notice: Subject to any disclaimer, the term of this patent is extended or adjusted under 35 U.S.C. 154(b) by 27 days.

(21) Appl. No.: 10/231,515

(22) Filed: Aug. 30, 2002

(65) Prior Publication Data

US 2003/0124577 A1     Jul. 3, 2003

Related U.S. Application Data

(60) Provisional application No. 60/316,367, filed on Aug. 31, 2001.

(51) Int. Cl.$^7$ .......................... C12O 1/68; C07H 21/04; C07H 21/00
(52) U.S. Cl. ........................ 435/6; 536/23.1; 536/24.3; 536/24.31; 536/25.32
(58) Field of Search .......................... 435/6, 91.1, 91.2; 536/23.1, 24.3, 24.33

(56) References Cited

OTHER PUBLICATIONS

Schulze et al. Navigating gene expression using microarrays-a technology review, Nature Cell Biology, vol. 3, pp. e190-e195, Aug. 1, 2001.*
Watts et al. Molecular profiling of cells from carriers of the ATM mutations. European Journal of Human Genetics, vol. 9, Supplement 1, pp C068, Conference Abstract, May 15-19, 2001.*
Chen et al. Expression profiling in the Muscular Dystrophies: Identification of Novel Aspects of Molecular Pathophysiology, vol. 151, No. 6, pp. 1321-1336, Dec. 11, 2000.*
Savitsky, K. et al. "A single ataxia telangiectasia gene with a product similar to PI-3 kinas"; Science, 268(5218): 1749-1753 (1995).
Tusher, V.G. et al. "Significance anaylsis of microarrays applied to the ionizing radiation response"; PNAS, 98(9): 5116-5121 (2001).
Lee, M.T. et al. "Importance of replication in microarray gene expression studies: Statistical methods and evidence from repetitive cDNA hybridizations"; PNAS, 97(18): 9834-9839 (2000).
Shigeta, T. et al. "Defective Control of Apoptosis and Mitotic Spindle Checkpoint in Heterozygous Carriers of ATM Mutation"; Cancer Research, 59: 2602-2607 (1999).
Barlow, C. et al. "Atm haploinsufficiency results in increased sensitivity to sublethal doses of ionizing radiation in mice"; 21: Nature Genetics, 21: 359-360 (1999).
West, C.M.L. et al. "A comparison of the radiosensitivity of lymphocytes from normal donors, cancer patients, individuals with ataxia-telangiectasia (A-T) and A-T heterozygotes"; Int. J. Radiat. Biol., 68(2): 197-203 (1995).
Alizadeh, A.A. et al. "Distinct types of diffuse large B-cell lymphoma identified by gene expression profiling"; Nature, 403: 503-511 (2000).
Perou, C.M. et al. "Molecular portraits of human breast tumours"; Nature, 406: 747-752 (2000).
Bittner, M. et al. "Molecular classification of cutaneous malignant melanoma by gene expression profiling"; Nature, 406: 536-540 (2000).
Golub, T.R. et al. "Molecular Classification of Cancer: Class Discovery and Class Prediction by Gene Expression Monitoring"; Science, 286: 531-537 (1999).
Concannon, P. et al. "Diversity of ATM Gene Mutations Detected in Patients With Ataxia-telangiectasia"; Human Mutation, 10: 100-107 (1997).
Gilad, S. et al. "Ataxia-telangiectasia: founder effect among North African Jews"; Human Molecular Genetics, 5(12): 2033-2037 (1996).
Broeks, A. et al. "ATM-Heterozygous Germline Mutations Contribute to Breast Cancer-Susceptibility"; Am. J. Hum. Genet., 66: 494-500 (2000).
Athma, P. et al. "Molecular Genotyping Shows That Ataxia-Telangiectasia Heterozygotes Are Predisposed to Breast Cancer"; Cancer Genet Cytogenet, 92: 130-134 (1996).
Paterson, M.C. et al. "Enhanced Radiosensitivity of Cultured Fibroblasts from Ataxia Telangiectasia Heterozygotes Manifested by Defective Colony-forming Ability and Reduced DNA Repair Replication after Hypoxic γ-Irradiation"; Cancer Research, 39: 3725-3734 (1979).
Telatar, M. et al. "Ataxia-Telangiectasia: Mutations in ATM cDNA Detected by Protein-Truncation Screening"; Am. J. Hum. Genet., 59: 40-44 (1996).
Swift, M. et al. "Incidence of Cancer in 161 Families Affected by Ataxia-Telangiectasia"; New England Journal of Medicine, 325(26): 1831-1836 (1991).
Wright, J. et al. "A High Frequency of Distinct ATM Gene Mutations in Ataxia-Telangiectasia"; Am. J. Hum. Genet., 59: 839-846 (1996).
Liu, V.F. et al. "The Ionizing Radiation-Induced Replication Protein A Phosphorylation Response Differs between Ataxia-Telangiectasia and Normal Human Cells", Molecular and Cellular Biology, 13(12): 7222-7231 (1993).
Weeks, D.E. et al. "Assessment of Chronic γ Radiosensitivity as an in Vitro Assay for Heterozygote Identification of Ataxia-Telangiectasia"; Radiation Research, 128: 90-99 (1991).

* cited by examiner

*Primary Examiner*—Gary Benzion
*Assistant Examiner*—Cynthia Wilder
(74) *Attorney, Agent, or Firm*—Dann, Dorfman, Herrell and Skillman; Kathleen D. Rigaut

(57) ABSTRACT

Novel methods are provided for identifying heterozygous carriers of autosomal recessive disorders such as Ataxia telangiectasia.

7 Claims, 3 Drawing Sheets

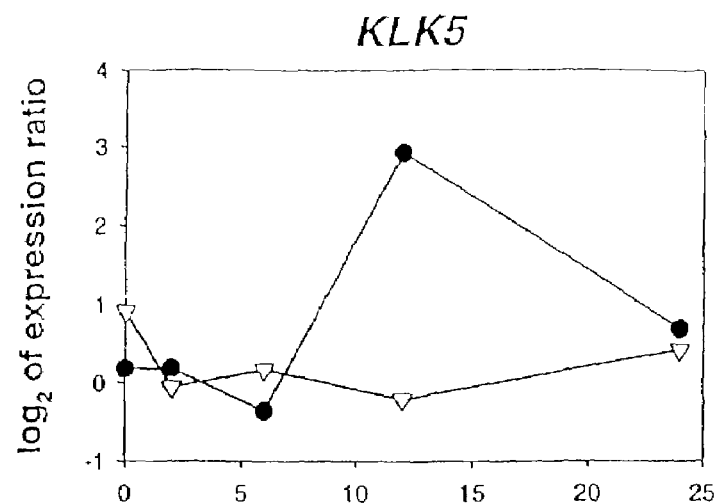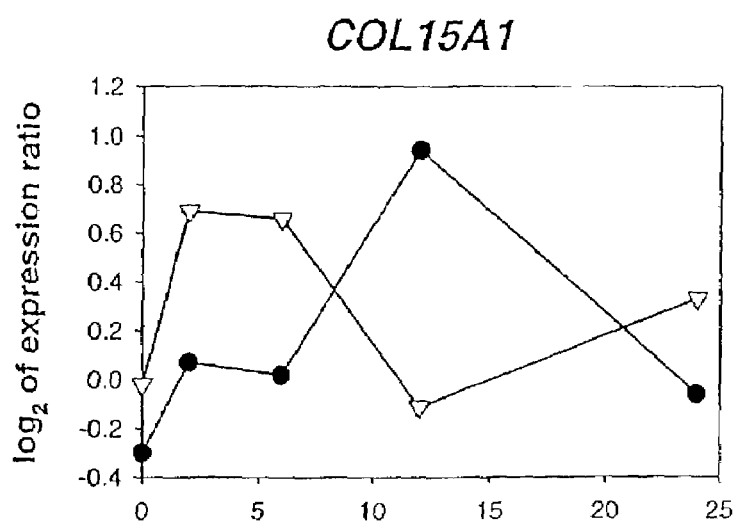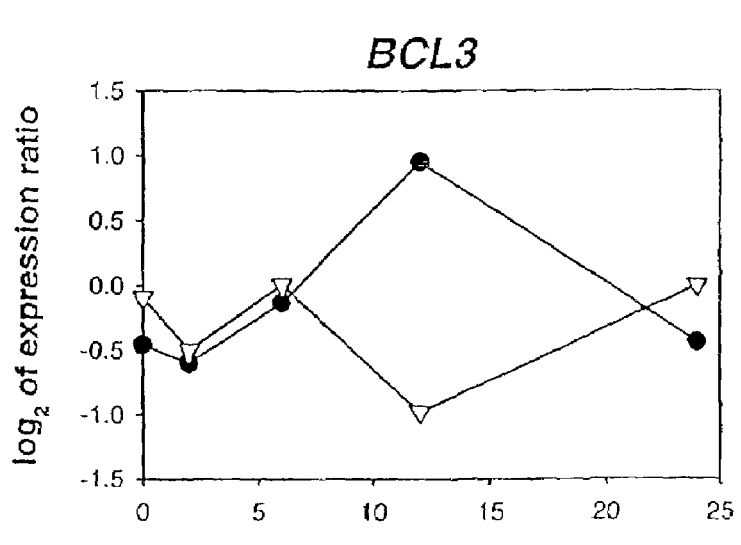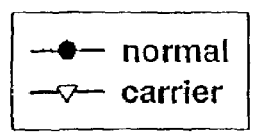

METHODS FOR IDENTIFYING HETEROZYGOUS CARRIERS OF AUTOSOMAL RECESSIVE DISEASES

This application claims priority to U.S. Provisional Application No. 60/316,367 filed Aug. 31, 2001, the entire disclosure of which is incorporated by reference herein.

Pursuant to 35 U.S.C. Section 202(c), it is acknowledged that the United States Government has certain rights in the invention described herein, which was made in part with funds from the National Institutes of Health, Grant Nos. DC00154, HG01880, DK55227 and DK46618.

FIELD OF THE INVENTION

This invention relates generally to DNA microarray technology, and more specifically to methods for identifying heterozygous carriers of autosomal recessive diseases, Ataxia telangiectasia being exemplified herein.

BACKGROUND OF THE INVENTION

Several publications and patent are referenced in this application by author name and year of publication in parentheses in order to more fully describe the state of the art to which this invention pertains. Full citations for these references are found at the end of the specification. The disclosure of each of these publications and patent documents is incorporated by reference herein.

Ataxia telangiectasia (AT) is an autosomal recessive disease caused by mutations in the gene, ataxia telangiectasia mutated (ATM), on human chromosome 11q21 (Savitsky et al, 1995). The ATM product is a protein kinase that plays a role in DNA damage repair through cell cycle regulation. AT is a rare disease, with a frequency of approximately $1/40,000$ individuals. The corresponding frequency of heterozygous carriers is about $1/100$. Although AT is a recessive disease, epidemiological studies have shown that AT carriers have shortened lifespans and elevated risks for cancer, especially breast cancer. Cellular studies have also shown that heterozygous carriers of AT have an increased sensitivity to ionizing irradiation (IR) (Swift et al, 1986; Swift et al, 1991; Athma et al, 1996; Broeks et al, 2000). Some reports have estimated that AT carriers have a 5-fold increase in risk for breast cancer compared to normal controls and may account for 8–18% of all breast cancer patients in the United States (Swift et al, 1976).

Despite the importance of detecting AT carriers, there is no precise diagnostic assay for identifying them. ATM is a large gene (approximately 150 kb) and has no common mutations which makes it difficult to design sequence-based diagnostic methods for identifying carriers of AT (Gilad et al, 1996; Wright et al, 1996; Concannon & Gatti, 1997). In addition, existing protein and cell-based assays are inaccurate for identifying heterozygous carriers, and are also time- and labor-intensive (Telatar et al, 1996). Nevertheless, a reliable method for identifying AT carriers will make it possible to establish the risk of radiation-induced cancer and to develop safety guidelines for radiation-based diagnostic procedures and therapies.

SUMMARY OF THE INVENTION

In accordance with the present invention, a novel method for identifying heterozygous carriers of autosomal recessive disorders is provided. The method comprises identifying a genetic signature for heterozygous carriers of autosomal recessive disorders by obtaining nucleic acid samples from cells of heterozygous carriers and normal individuals, generating detectably labeled probes from these nucleic acid samples, contacting cDNA microarrays with the detectably labeled probes under conditions that facilitate hybridization between complementary nucleic acids, analyzing the cDNA microarrays for cDNA hybrids, and comparing the hybridization profiles from the heterozygous carriers and normal individuals to generate a genetic signature. The genetic signature (consisting of a plurality of differentially expressed genes) differentiates carriers of an autosomal recessive disorder from normal controls.

The method of the invention may be used to identify heterozygous carriers of such autosomal recessive disorders including, but not limited to Ataxia telangiectasia, Cystic Fibrosis (CF), Sickle Cell Anemia, Tay-Sachs disease, Phenylketonuria (PKU), Oculocutaneous Albinism (OCA), Hereditary Haemochromatosis (HH), AAT deficiency, ADA deficiency, β-thalassemia, alpha-1 antitrypsin deficiency, Spinal Muscular Atrophy, Friedreich's Ataxia, and Congenital Adrenal Hyperplasia.

In accordance with another aspect of the invention, a genetic signature is provided for identifying heterozygous carriers of Ataxia telangiectasia. The genetic signature comprises at least 4 of the nucleic acid sequences set forth in Table I.

BRIEF DESCRIPTION OF THE DRAWINGS

FIGS. 2A–2E shows graphs mapping the time-course of gene expression after exposure to IR (3 Gy). Expression levels were determined using pooled RNA from 7 AT carriers and 6 normal individuals.

DETAILED DESCRIPTION OF THE INVENTION

Figure 1:
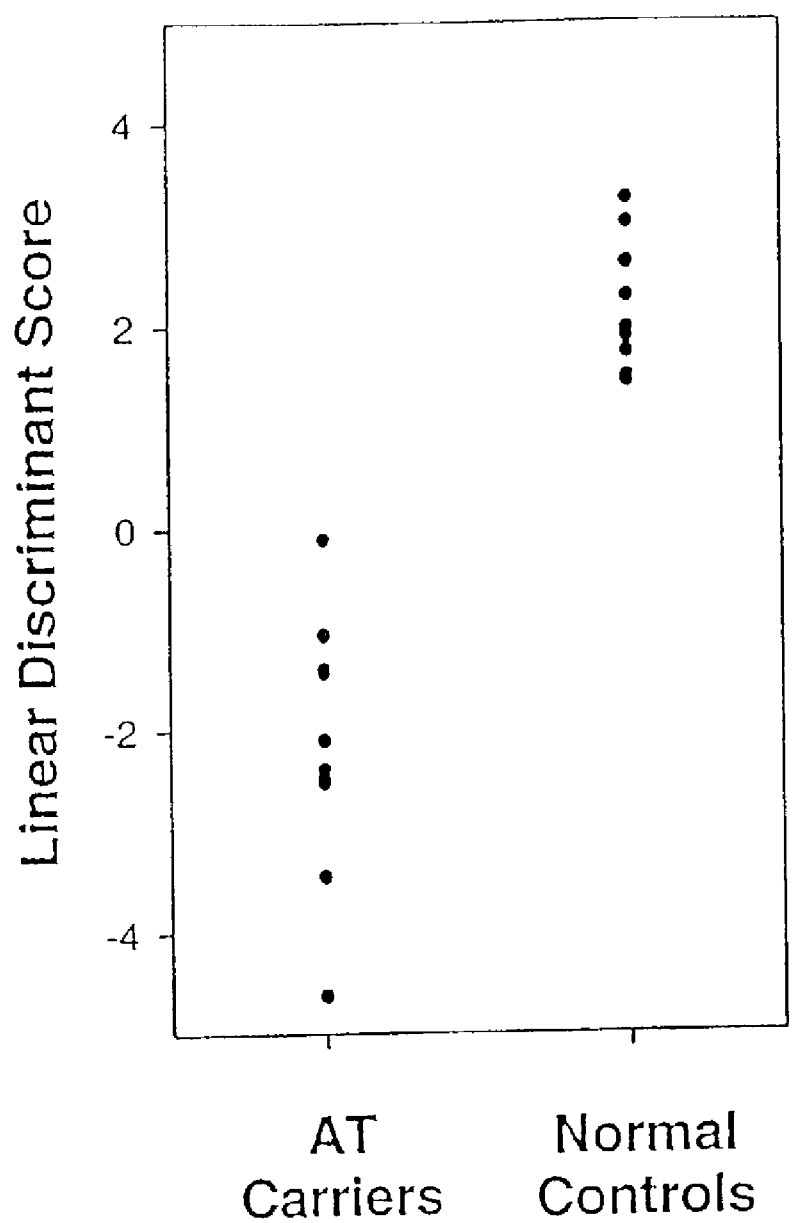
FIG. 1 shows a graph of the discriminate scores for gene expression levels in cells from 10 AT carriers and 10 normal individuals. Four genes (LIM, CDKN2, TFRC, and ARF6) were selected by stepwise linear discriminate analysis.
Figures 2D, 2E:
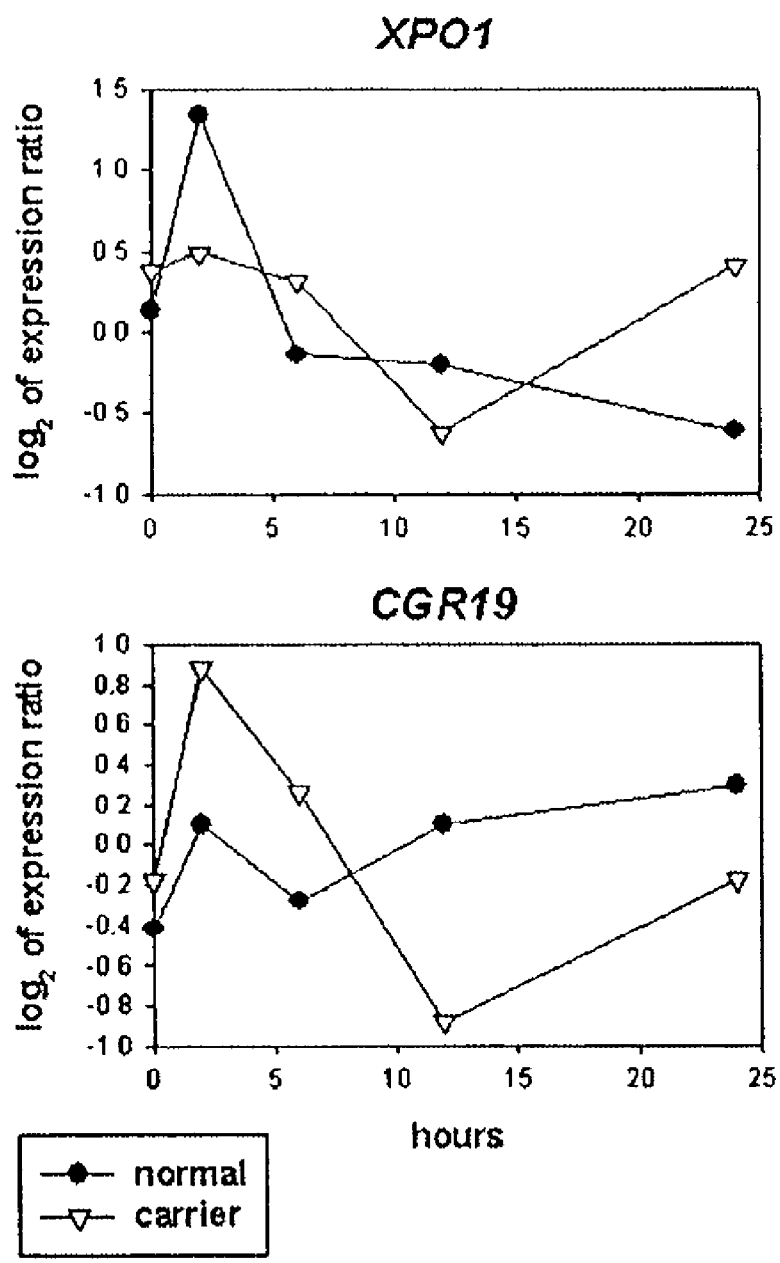

The classical definition of an autosomal disease is one where the phenotypic effect is not expressed in the heterozygous carriers. However, close scrutiny may reveal that heterozygotes have subtle phenotypic differences from normal individuals. One example is the autosomal recessive disease, ataxia telangiectasia (AT), which is caused by mutations in the gene, ataxia telangiectasia mutated (ATM). Heterozygous carriers for AT have one mutated copy of the ATM gene.

Epidemiological studies have suggested that carriers for this recessive disease have an increased risk for various other diseases, especially breast cancer. Therefore, an accurate method for identifying AT carriers from normal individuals would be extremely beneficial for early diagnosis and prevention of cancer in these individuals, as well as an invaluable genetic tool for identifying heterozygous carriers of various other autosomal recessive disorders throughout a given population.

Thus, in accordance with one aspect of the present invention, a novel method for identifying AT carriers from normal individuals was developed using cDNA microarrays to identify genes which exhibit altered expression levels between AT carriers and normal individuals. The results provide a genetic tool for identifying AT carriers, and may also facilitate the elucidation of the molecular mechanisms controlling the pathogenesis of radiation-induced malignancies in this at-risk group.

In accordance with another aspect of the invention, methods are provided which may be used to advantage to identify heterozygous carriers of any other autosomal recessive disorders including, but not limited to Cystic Fibrosis (CF), Sickle Cell Anemia, Tay-Sachs disease, Phenylketonuria (PKU), Oculocutaneous Albinism (OCA), Hereditary Haemochromatosis (HH), AAT deficiency, ADA deficiency, β-thalassemia, alpha-1 antitrypsin deficiency, Spinal Muscular Atrophy, Friedreich's Atoxia, and Congenital Adrenal Hyperplasia.

I. Definitions

The following definitions are provided to facilitate an understanding of the present invention:

With reference to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. An "isolated nucleic acid molecule" may also comprise a cDNA molecule or a recombinant nucleic acid molecule.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

The term "oligonucleotide," as used herein refers to sequences and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., 1989):

$$T_m = 81.5° \text{ C.} + 16.6\text{Log}[Na+] + 0.41(\% \ G+C) - 0.63(\% \text{ formamide}) - 600/\#bp \text{ in duplex}$$

As an illustration of the above formula, using [Na+]=[0.368] and 50% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C.

The term "probe" as used herein refers to an oligonucleotide, polynucleotide or DNA molecule, whether occurring naturally as in a purified restriction enzyme digest or produced synthetically, which is capable of annealing with or specifically hybridizing to a nucleic acid with sequences complementary to the probe. The probes of the present invention refer specifically to the oligonucleotides attached to a solid support in the DNA microarray apparatus such as the glass slide. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15–25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to a DNA oligonucleotide, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15–25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

The term "specific binding pair" as used herein includes antigen-antibody, receptor-hormone, receptor-ligand, agonist-antagonist, lectin-carbohydrate, nucleic acid (RNA or DNA) hybridizing sequences, Fc receptor or mouse IgG-protein A, avidin-biotin, streptavidin-biotin, amine-reactive agent-amine conjugated molecule and thiol-gold interactions. Various other determinant-specific binding substance combinations are contemplated for use in practicing the methods of this invention, such as will be apparent to those skilled in the art.

The term "detectably label" is used herein to refer to any substance whose detection or measurement, either directly or indirectly, by physical or chemical means, is indicative of the presence of the target bioentity in the test sample. Representative examples of useful detectable labels, include, but are not limited to the following: molecules or ions directly or indirectly detectable based on light absorbance, fluorescence, reflectance, light scatter, phosphorescence, or luminescence properties; molecules or ions detectable by their radioactive properties; molecules or ions detectable by their nuclear magnetic resonance or paramagnetic properties. Included among the group of molecules indirectly detectable based on light absorbance or fluorescence, for example, are various enzymes which cause appropriate substrates to convert, e.g., from non-light absorbing to light absorbing molecules, or from non-fluorescent to fluorescent molecules.

Polymerase chain reaction (PCR) has been described in U.S. Pat. Nos. 4,683,195, 4,800,195, and 4,965,188, the entire disclosures of which are incorporated by reference herein.

The phrase "obligate carrier" refers to an individual who is a heterozygous carrier of a gene associated with an autosomal recessive disorder.

II. cDNA Microarrays

Exemplary cDNA microarrays of the invention are commercially available and may be purchased from such companies as Agilent Technologies, Affymetrix Inc. (Santa Clara, Calif.), Nanogen (San Diego, Calif.) and Protogene Laboratories (Palo Alto, Calif.).

In a preferred embodiment of the invention, cDNA microarrays were prepared on aminoalkylsilane coated microscope slides (Sigma, St Louis, Mo.) using a pin-and-ring arrayer (Affymetrix 417, Bedford, Mass.).

The following examples provide illustrative methods of practicing the instant invention, and are not intended to limit the scope of the invention in any way.

EXAMPLE 1

Expression Analysis Reveals Cellular Phenotype of Heterozygous Carriers of ATM Mutations Using cDNA microarrays to monitor gene expression levels, it was determined that alterations in gene expression patterns differentiate heterozygous carriers of Ataxia Telangiectasia (AT) from normal individuals. The differences are manifested in both baseline expression levels and in response to ionizing radiation (IR). These findings provide a novel approach to diagnose AT carriers and may also facilitate an understanding of the molecular basis of their increased risk to cancer.

I. Materials and Methods:

The following protocols are provided to facilitate the practice of the present invention.

Baseline Expression Levels:

Lymphoblastoid cell lines were obtained from 10 obligate AT carriers (GM08931, GM03334, GM03382, GM03188, GM09588, GM00736, GM02781, GM09585, GM09583, GM09579) and 10 normal control individuals (GM06995, GM06997, GM07014, GM10832, GM10835, GM10848, GM10849, GM10860, GM06987, GM07038). None of the subjects were known to be blood relatives. Reference samples used in all hybridization reactions were made with RNA from 6 CEPH individuals (GM06987, GM07038, GM06995, GM06997, GM07014, GM07042). All of the cell lines were obtained from Coriell Cell Repositories (Camden, N.J.).

Expression Response to IR:

In the first experiment, lymphoblastoid cell lines from 7 obligate AT carriers (GM09583, GM09579, GM08930, GM08931, GM03334, GM03382, GM03188) and 6 normal controls (GM10832, GM10835, GM10860, GM10848, GM10849, GM07057) were studied. In the second round, lymphoblastoid cells lines from 5 new obligate AT carriers (GM00736, GM02781, GM03187, GM09585, GM09588) and 6 new normal controls (GM06987, GM07038, GM06995, GM06997, GM07014, GM07042) were used. None of the subjects were known blood relatives. Reference samples used in all hybridizations were made with RNA from 6 CEPH individuals. All the cell lines were obtained from Coriell Cell Repositories (Camden, N.J.).

cDNA Microarrays:

2,880 cDNA clones were randomly selected from a sequence-verified cDNA clone set (Research Genetics, Huntsville, Ala.). The clones were grown in LB-chloramphenicol as overnight cultures. The cultures were then diluted (1:10 dilution with TE), boiled at 95° C. for 3 minutes and used as DNA templates for PCR amplifications. DNA was amplified with 0.4 uM vector specific primers (T3/T7 or M13 forward and reverse), 200 uM dNTP, 2.5 mM $MgCl_2$, 2.5U Taq DNA polymerase (Perkin-Elmer or Promega) and 1×PCR buffer. Amplifications were carried out in 96-well plates with an initial denaturation at 96° C. for 5 minutes, followed by 30 cycles of 94° C. for 30 seconds, 55° C. for 30 seconds, 72° C. for 30 seconds and a final extension at 72° C. for 5 minutes. Ten percent of the amplicons in each 96-well plate were checked by gel electrophoresis. If the success rate of amplifications was 90% or greater, the amplicons were ethanol precipitated and dried; otherwise, the amplifications were repeated. The amplicons were then reconstituted in 2×SSC, 0.01% sarkosyl for arraying onto aminoalkylsilane coated microscope slides (Sigma, St Louis, Mo.) using a pin-and-ring arrayer (Affymetrix 417, Bedford, Mass.).

The DNA samples on the array were moistened over gentle steam and UV-crosslinked for attachment onto the glass surface. The glass arrays were denatured at 95° C. for 3 minutes and then immediately placed into ice-cold ethanol. The arrays were then dried by centrifugation at 3000 rpm for 2 minutes. The arrays were then prehybridized with 5×SSC, 0.2% SDS, 1% BSA at 42° C. for 1 hour.

Probe Preparation:

EBV-transformed lymphoblastoid cells were grown in RPMI 1640 medium with 15% fetal bovine serum, 1% penicillin, 1% streptomycin, 1% L-glutamine at 37° C. in a humidified 5% $CO_2$ chamber. Cells were grown to a density of ~1×10⁶/ml. They were irradiated with 3 Gy ionizing radiation in a $^{137}Cs$ gamma irradiator. To minimize variations caused by culture conditions, all cells were irradiated 24 hours after addition of fresh medium. The cells were harvested before irradiation and also at 2, 6, 12, and 24 hours post-irradiation. Total RNA was extracted from cell pellets using the RNeasy midi kit (Qiagen, Germany).

In each reaction, total RNA was reverse transcribed into fluorescently (Cy3 or Cy5) labeled cDNA using the Genisphere 3DNA expression array detection kit (Genisphere, Montvale, N.J.). Briefly, for each reaction, 10 $\mu$g total RNA was reverse transcribed using 1 pM oligo dT-Genisphere capture primer, 0.5 mM dNTP, 200U Superscript II (Gibco BRL) in 1×first strand Superscript II buffer at 42° C. for 2 hours. The RNA from the DNA/RNA hybrids was denatured with 0.07 M NaOH. The reaction was then neutralized to pH 7.5 using Tris-HCl. For each array hybridization, 10% of the cDNA mixture was incubated with 2.5 $\mu$l Cy3 or Cy5 dendrimer in Expresshyb (Clontech) at 55° C. for 30 minutes. Two $\mu$g of denatured $Cot_1DNA$ (Gibco BRL) was added and the entire mixture was added onto the prehybridized array for hybridization at 62° C. for at least 12 hours. After hybridization, the arrays were washed with 2×SSC, 0.2% SDS at 55° C. for 7 minutes, followed by a wash with 2×SSC and another with 0.2×SSC at room temperature for 7 minutes each. The hybridization signals were read using a dual-laser fluorescent scanner (Affymetrix 418, Bedford, Mass.).

Analysis of Replicated Microarrays:

The cDNA microarrays were scanned using a Spotfinder (TIGR, www.tigr.org). For each data point (or observation), the hybridization signals from the image analysis yielded values (or signal intensity) for Cy3 (experimental) and Cy5 (reference). The Spotfinder assigned a signal intensity of 0 to an observation when the signal was less than the background. If the Cy5 value was zero, that observation was not included in the analysis. Signal intensities for the Cy3 and the Cy5 channels were "normalized" and the Cy3 measurements were multiplied by a scaling factor to make the mean Cy3/Cy5 ratio for all the spots on the slide equal to 1.0. (Assume on average that the genes have the same expression level in the experimental and the reference samples.) The Cy3 value was then divided by the Cy5 value to generate the expression ratio R for each replicate of each gene.

It was particularly necessary to deal appropriately with data for genes that were expressed in some individuals but not in others. The Cy3 value (and R) for these genes were 0 for some arrays. To calculate the logarithm of the expression ratio, the R values that were 0 were replaced with R', the smallest non-zero R found for any gene on that slide. The transformation of the observations were then completed by calculating $log_2$ of the R and R' values.

Replicates:

Each hybridization reaction was repeated four times. The analysis was performed on each hybridization reaction that included three or more replicate observations. The goal was to eliminate single observations that were "aberrant" for technical reasons, and retain only those observations that were valid.

For some genes, individual replicate observations were discarded because the Cy5 value for that replicate was 0. If fewer than 3 replicate observations remained, that gene was discarded from the analysis. If all four values remained, the replicate value that was most deviant from the mean of the replicates was discarded. This "trimming" was not performed if there were only three valid observations.

The rest of the analysis was carried out with the remaining three observations for each hybridization reaction. For each gene, the mean of the remaining replicate observations was calculated and used for further analysis.

Baseline Experiments:

To analyze the microarray data, the t statistic was chosen because of its familiar properties, and was used solely as a measure of the difference between carriers and controls in gene expression levels, not for a "t-test" (Callow et al. 2000; Tusher et al. 2001). In order to determine whether there were more differences between carriers and controls than expected by chance, we used a permutation test as follows (Manly 1997). We assigned each individual (with complete set of values for 2880 genes) randomly to one of two groups of 10 (corresponding to the real sample sizes); we then calculated the t-score (absolute value) for each gene. After repeating this procedure 3,000 times, we had a distribution of t-scores for each gene based on the 20 values actually observed for expression level but with group membership randomized.

For each gene, we determined whether the t-score (absolute value) from the real data fell among the largest 1% of values resulting from permutation. When several t-scores among the 3,000 had the same value, we assigned the percentile of the real value(conservatively) as the least extreme in the set. Among the 2,880 genes/ESTs on the array, there were 71 whose t-scores fell in the largest 1% obtained from permutation. Similarly, we used the 3,000 sets of permutations to provide 3,000 estimates for the number of extreme t-scores expected under the null hypothesis that no genes differ in expression level between carriers and controls. The frequency of permutations in which this number was 71 or greater (14/3,000 in our case) is our estimate of the significance level for rejecting the null hypothesis.

Conventional stepwise linear discriminate analysis (SPSS; Chicago, Ill.) was carried out with data from the 12 genes with observations on all 20 individuals and identified the four genes named in the text. Adding genes beyond the four selected did not yield discrimination that was significantly better (at P<0.05 level). Assignment to the two groups was performed with the "leave-one-out" cross-validation procedure.

IR Response (Time-course) Experiment

Standardization over experiments was carried out as follows. For each time-point, the set of observations for all genes was considered separately for carriers (pooled RNA) and normal controls (pooled RNA). Most of the cell lines for the IR response experiment were from individuals used previously in the baseline experiment. The mean and standard deviation were determined (for that time-point), and each observation was expressed as units of standard deviation from the mean for all genes.

Discriminate analysis was carried out on the standardized expression ratios for only the genes that had valid observations at all the time-points, using the statistical package SPSS. The variables are the expression levels at five time-points after irradiation. These were measured on the 2880 genes ("members" of the carrier group) in one RNA sample pooled from carriers. The same five variables were measured on 2880 genes (the "members" of the control group) in pooled RNA from controls. Thus, the carrier and control groups consist of gene expression observations on the same set of genes, but in different pools of RNA. The discriminate function was estimated using the pooled covariance matrix for carriers and controls. The discriminate score (linear combination of five observations) for each gene in each group was used to assign gene expression pattern to one of the two groups (with cross-validation). For each gene, two expression patterns were assigned, one with the observations from carriers, one with those from normal controls. This approach detects the genes with the most different levels of expression after irradiation, but does not directly address differences in time trends.

In the first experiment, this procedure resulted in 442 genes correctly assigned for both groups; in the replication experiment, this resulted in 183 (of the 442) genes correctly assigned for both groups. To identify particular genes with the most distinctive expression patterns, we compared the discriminate scores for assigning each gene to the carrier or the normal control group. Genes were ranked by the difference in these two scores. This was done for the first and the replication experiments, and the mean of the two values was found. The genes with largest mean difference are taken to be those with most distinctive expression patterns.

Real-time Quantitative RT-PCR

Five of the 183 genes that were correctly assigned in the time-course experiments were assayed using real-time quantitative RT-PCR. Sequences of these genes were obtained from UCSC Genome Browser. Primers were designed using Primer Express software (Applied Biosystems, Calif.). The reactions were performed with 1×SYBR-Green PCR master mix buffer (Applied Biosystems, Calif.), 300 nM forward and reverse primers and cDNA. cDNA from lymphoblastoid cell lines from 2 AT carriers (GM09585, GM09588) and 2 normal controls (GM06987, GM06997) was analyzed. Assays were performed in triplicate using an ABI 7000 instrument. The fold change was calculated using a standard curve analysis and normalized to the level of B-actin. For each gene, the data from the two AT carriers were averaged as were those from the two normal controls. These results from RT-PCR were compared to the corresponding microarray results by calculating the correlation coefficient of the expression ratio over the five time-points.

II. Results

Baseline Expression Differences cDNA microarrays were used to compare the expression levels of genes in lymphoblastoid cells from 10 AT carriers and 10 normal controls. The Cy3-labeled cDNA from each individual was co-hybridized with the Cy5 reference cDNA onto microarrays containing ~3,000 human known genes/ESTs. All hybridizations were done with four replicates. We removed the most deviant observation from every set of four replicates and represented the expression level of each gene by the average of the three remaining measurements (see Analysis of Replicated Microarrays in Methods).

In this "baseline" experiment, we used the t statistic to compare the expression level of each gene in cells from AT carriers and normal controls. Our goal was to show that there are statistically significant differences between carriers and controls in the number of genes that differ in expression level, and to identify the genes that are most likely to show consistent differences. We assessed the significance of the t-scores for each gene empirically by a permutation test. Among the 2,880 cDNA clones on the arrays, we found 71 clones whose t-scores ranked in the top 1% of the 3,000 random permutations we carried out with the data from the 10 AT carriers and 10 normal controls; the absolute values of these t-scores ranged from 1.6 to 5.1. Because of the large number of tests, the corresponding P-values of ≦0.01 are "nominal"; nevertheless, the true significance of the number of genes (71 clones) can be assessed, as follows.

To determine the statistical significance of our overall result, we used the permutations described above. These provided 3,000 estimates for the number of genes with nominal P≦0.01L by chance, i.e., under the null hypothesis that no gene among the 2,880 differs significantly between carriers and controls. Among the 3,000 permutations, we found only 14 permutations (0.47%) with 71 or more clones that met this criterion. The mean number of genes from the permutations was 27.4. We conclude that there are significantly (P≦0.005) more genes that differ in baseline expression level than expected under the null hypothesis.

Among the 71 clones, 29 are known genes (WEE1 is represented by two clones) and 41 are ESTs. We list the 29 known genes (represented by 30 cDNA clones) in Table 1. Among them, 15 genes (HDAC1, MAPKAP3, WEE1, LIM, CDKN2D, THBS1, SSI2, TSSC6, CCNE1, CHN2, G6PD, TXN2, RPA1, GCP3, DIO1) regulate cell growth and maintenance through various pathways, including cell cycle control and regulation of apoptosis (Heald et al. 1993; Liu and Weaver 1993; McLaughlin et al. 1996; Roberts 1996; Minamoto et al. 1997; Ueno et al. 1999; Ashburner 2000; Juan et al. 2000; Tuttle et al. 2000). Table 1 shows the t-score and the P-value for each known gene.

TABLE 1

The 30 cDNA clones (representing 29 known genes) with largest difference (nominal P < 0.01 by permutation test) in baseline expression level between AT carriers and normal controls.

| Gene | Gene Name | Degrees of Freedom | T-score (Carrier-control) | P-value* |
|---|---|---|---|---|
| CSF2RA | Colony stimulating factor 2 receptor alpha | 9 | 2.85 | <0.0003 |
| HDAC1 | Histone deacetylase 1 | 12 | −3.30 | <0.0003 |
| MAPKAPK3 | MAP kinase-activated protein kinase 3 | 14 | −3.04 | <0.0003 |
| SLC25A6 | Solute carrier family 25, member 6 | 18 | 3.61 | <0.0003 |
| WEE1 | WEE1 | 18 | −3.37 | 0.0003 |
| TFRC | Transferrin receptor (p90) | 18 | −3.15 | 0.0007 |
| LIM | LIM protein | 18 | 3.81 | 0.0010 |
| OGT | O-linked N-acetyl-glucosamine transferase | 15 | 2.18 | 0.0010 |
| WEE1 | WEE1 | 16 | −3.20 | 0.0010 |
| CDKN2D | Cyclin-dependent kinase inhibitor 2D (p19) | 18 | −3.31 | 0.0013 |
| THBS1 | Thrombospondin 1 | 17 | 3.57 | 0.0013 |
| SSI2 | STAT induced STAT inhibitor | 16 | 3.77 | 0.0023 |
| TSSC6 | Pan-hematopoietic expression | 14 | 3.76 | 0.0023 |
| CCNE1 | Cyclin E1 | 13 | −2.57 | 0.0027 |
| CHN2 | Chimerin | 18 | −3.14 | 0.0030 |
| G6PD | Glucose-6-phosphate dehydrogenase | 17 | 3.80 | 0.0033 |
| PLOD3 | Procollagen-lysine, 2-oxoglutarate 5-dioxygenase 3 | 17 | −3.27 | 0.0033 |
| TXN2 | Thioredoxin | 16 | 3.27 | 0.0037 |
| ARF6 | ADP-ribosylation factor 6 | 18 | −2.98 | 0.0047 |
| CSF3R | Colony stimulating factor 3 receptor | 16 | −2.14 | 0.0047 |
| NDST1 | N-deacetylase 1 | 15 | 3.22 | 0.0047 |
| GOSR2 | Golgi SNAP receptor complex member 2 | 13 | −3.00 | 0.0053 |

TABLE 1-continued

The 30 cDNA clones (representing 29 known genes) with largest difference (nominal P < 0.01 by permutation test) in baseline expression level between AT carriers and normal controls.

| Gene | Gene Name | Degrees of Freedom | T-score (Carrier-control) | P-value* |
|------|-----------|--------------------|---------------------------|----------|
| KIAA0204 | Ste20-related serine/threonine kinase | 11 | −2.35 | 0.0057 |
| RPA1 | Replication protein A1 | 17 | −2.19 | 0.0060 |
| GCP3 | Spindle pole body protein 3 | 16 | 1.98 | 0.0067 |
| SULT1C1 | Sulfotransferase family, 1C, member 1 | 13 | 3.04 | 0.0073 |
| HNRPD | Heterogeneous nuclear ribonucleo-protein D | 15 | −3.27 | 0.0080 |
| DIO1 | Death inducer-obliterator 1 | 12 | −2.86 | 0.0083 |
| SLC7A6 | Solute carrier family 7, member 6 | 7 | 3.01 | 0.0083 |
| PPP1R2 | Protein phosphatase 1, regulatory subunit 2 | 17 | −2.97 | 0.0097 |

*Genes are ranked by P-value.

The most marked excess of small permutation P-values occurs for the 22 clones with P-values smaller than 0.0017. This observation suggests that these genes and ESTs are the most likely to be "true positives."

Classification of AT Carriers and Normal Individuals

To explore the biological differences between AT carriers and normal controls, we wanted to identify the largest set of genes that differ in expression between the two groups. However, for classification purposes, we want to have the smallest set of genes whose expression levels when combined in a discriminate procedure would yield highly accurate classification. To find that set, we carried out discriminate analysis with a subset of the 71 clones with nominal P≦0.01. In the analysis, we used the 12 genes/ ESTs for which we have expression values in all 20 individuals. By stepwise discriminate analysis, we selected four genes (LIM, CDKN2D, TFRC, and ARF6) and determined the best linear discriminate function. The discriminate scores for the 10 AT carriers and 10 normal controls are shown in FIG. 1. The apparent greater variance in carriers is not surprising, in view of the known heterogeneity of AT mutations. However, the two distributions do not overlap so the discriminate function provides highly accurate assignment of these 20 individuals to the two groups. We also assessed how accurately we would classify individuals who were not part of the "training" sample. For this purpose, we carried out "cross-validation;" the individual to be assigned was left out of both the selection of genes and calculation of the discriminate function, and then was assigned on the basis of the data from the other 19 individuals. Of the 20 cross-validation "trials," nine resulted in exactly the same set of four genes as reported in the complete data. In the other 11, LIM in five, CDKN2D was included in nine, TFRC in ten and ARF6 in six trials. These findings indicate the tendency for the four genes to be selected even in cross-validation.

Since the 12 genes/ESTs in the starting set were selected from those with the largest t-scores, the high level of accurate classification for these 20 individuals is not surprising. Our purpose was not to show that classification is possible, but confirm that it can be achieved with a small number of genes and ESTs.

Differences in Transcriptional Response to Ionizing Radiation

In view of the increased sensitivity of AT patients to ionizing radiation (IR), we also studied the changes in expression profiles of AT carriers in response to IR. Lymphoblastoid cells from AT carriers and normal controls were exposed to low-dose radiation (3 Gy). In the "baseline" experiment above, we tested expression profiles of individuals. In order to reduce the number of hybridizations in this time-course experiment, we used pooled RNA samples instead of samples from individuals. This allowed us to obtain expression profiles at five time-points, instead of one time-point as in the previous experiment, and nevertheless continue our rigorous quality control by performing four replications of all array hybridizations. Lymphoblastoid cells from seven AT carriers and six normal controls were studied. Cells were harvested immediately before IR, and 2, 6, 12, and 24 hours post IR (3 Gy). At each time, total RNA was extracted from the cells and assembled into two pools, one from AT carriers and another from normal controls. Each pooled RNA sample was reverse-transcribed with Cy3 fluorescent tags into labeled cDNA. The Cy3-labeled AT carrier cDNA and the Cy3-labeled normal cDNA were separately hybridized with a common Cy5-labeled reference cDNA onto microarrays containing ~3,000 human genes/ESTs. Thus, there were two kinds of hybridization (AT carriers and normal) for each of the five time-points. All the hybridizations were carried out with four replicates. The replicate measurements were treated as above by removing the most deviant observations and carrying out the analysis on the remaining three measurements.

Our goal was to identify the genes that differ most between AT carriers and normal controls in expression levels at several time-points after irradiation. This is done to reveal the biological differences between AT carriers and normal controls and not for classification purposes. The discriminate analysis procedure allows us to replace the set of five observations on each gene by a single discriminate score; this score is used to assign the expression pattern of a gene to the carrier or the normal control group. Under our null hypothesis, we expect only random differences between the expression patterns of a gene tested in the two cell types. Thus, when tested in AT carriers, the expression pattern of a gene would have a 50% random chance of being correctly assigned as carrier; when the same gene is tested in normal cells, the expression pattern again would have 50% chance of being correctly assigned as normal. The random chance of correct assignment of the expression pattern in both cases together is 25%.

We analyzed only genes that gave three or four "valid" replicate observations at all five time-points in both cell types. In the first experiment, 1,382 cDNA clones met this criterion. Among these, the discriminate score (with cross-validation) correctly assigned 442 clones (32%) in both the AT carriers and normal controls; this is significantly higher than the 346 clones (25%) expected $x^2=36$; P<<0.001).

To follow up these results, we performed a replication experiment with just the 442 clones identified in the first experiment; we studied pools of RNA from five new AT carriers and six new normal controls. Among the 442 clones, there were 377 clones with valid observations (at least three replicates) at five time-points in both cell types. Among these 377 clones, 183 clones (48.5%) were assigned correctly in both groups, significantly more than the expected 94 clones (25%) under the null hypothesis $x^2=111$, P<<0.001). Thus, the expression differences between carriers and normal cells resulted in correct classification of approximately twice as many genes as expected by chance.

Thus by two successive rounds of classifications, we identified 183 clones whose expression levels over five time-points after IR are different between AT carriers and normal controls. Among these 183 cDNA clones, there were 101 uncharacterized ESTs and 82 known genes. When the 82 known genes were grouped into Gene Ontology categories, the two largest categories were cell growth and maintenance (25 genes; e.g., B-cell lymphoma 3—BCL3, Exportin 1—XPO1; Cell Growth Regulator 19—CGR19) and signal transduction (15 genes; e.g. Interferon receptor alpha 2, Jagged 2, IkappaB kinase complex associated protein). Compared to the proportions of genes in these categories present on the array (11% in cell growth/maintenance, 13% in signal transduction), the proportions observed are higher (P<0.001) for cell growth and maintenance. For illustration, we show the expression profiles of five genes (BCL3, XPO1, CGR19, KLK5 and COL15A1) from the cell growth and maintenance category in FIGS. 2A–2E. We expected some correct classification by chance (false positives). We ranked the 183 genes by the differences in discriminate scores between AT carriers and controls in the first and the replication studies. The top ranked genes are most likely to be true positives. Among the 183 genes, the 10 known genes with the largest differences in discriminate scores between AT carriers and controls are listed in order in Table 2. Independent confirmation of the microarray results was obtained by quantitative RT-PCR for five of the 183 genes: BCL3, CCN1, CHEK1, COL15A1, DAPK. For each gene, we calculated the correlation coefficient for the corresponding observations from microarrays and RT-PCR on cDNA from carriers and from controls. There was good agreement between the data from microarray and RT-PCR analysis. The average of the correlation coefficient was 0.76, with a range from 0.63 to 0.95.

TABLE II

| Gene Symbol | Gene Name | Function |
| --- | --- | --- |
| KLK5 | Kallikrein 5 | Protease |
| COL15A1 | Collagen, type XV, alpha 1 | Connective Tissue development and maintenance |
| BCL3 | B-cell CLL/lymphoma 3 | Cell cycle control |
| NRP2 | Neuropilin 2 | Receptor for semaphorins |
| KIAA0993 | unknown | |
| XPO1 | Exportin 1 | Cell cycle regulated nuclear export |
| IFNAR2 | Interferon (alpha, beta and omega) receptor 2 | Signal transduction |
| CGR19 | Cell growth regulatory with ring finger domain | Negative control of cell proliferation |
| MLF2 | Myeloid leukemia factor 2 | Cell growth |
| PCLB2 | phospholipase C β2 | hydrolyzes PIP 4,5, bisphosphate |

III. Discussion:

Diseases that result from single mutations can have many, apparently unrelated, manifestations (pleiotropy). AT patients, who have mutations in both copies of the ATM gene, have a wide variety of manifestations, from neurodegeneration and immune deficiency to malignancies. However, there is usually no marked heterozygote phenotype that permits identification of individual heterozygous carriers for a recessive disease. AT carriers as a group, who constitute about 1% of the population, have been shown by epidemiological studies to have a phenotype: increased cellular radiosensitivity and risk of cancer. However, the results described above demonstrate that the phenotype of AT carriers extends to marked differences in expression of many genes both at baseline and in response to low-dose ionizing radiation. DNA microarrays have been used successfully by others (Golub et al, 1999; Bittner et al, 2000; Alizadeh et al, 2000; Perou et al, 2000) to classify somatic mutations in cancers. The results presented herein further illustrate the effective use of DNA microarrays in classifying individual carriers of recessive germline mutations. The causes and pathogenesis of malignancies in AT carriers are very poorly understood. A major obstacle has been the lack of methods for correctly identifying carriers in the population. Here is was shown that AT carriers and normal individuals may be reliably distinguished by expression levels of 71 genes/ESTs at baseline, and by more than 180 gene expression patterns over five time-points after IR. When the baseline expression values of four (LIM, CDKN2, TFRC, ARF6) of the 71 genes were used together, 95% of the AT carriers and normal individuals were classified correctly. Thus, it is possible that the baseline expression values of some subset of the 71 genes reported here will allow the diagnosis of a great majority of carriers of ATM mutations.

To analyze the transcriptional response of carriers and normal controls to ionizing radiation, the multivariate differences were assessed by discriminate analysis. This functional analysis may help to explain why AT carriers are at increased risk for malignancies. Preliminary analyses showed that several known genes that were significantly different in baseline expression levels between AT carriers and normal individuals play a role in proliferation, apoptosis, and cell cycle regulation. These processes are critical in pathogenesis of cancer. Cellular assays have shown that cells from AT carriers have incomplete cell cycle arrest in response to IR, unlike normal cells (Paterson et al, 1979; West et al, 1995; Barlow et al, 1999; Xu & Baltimore, 1996; Shigeta et al, 1999). The data presented herein agreed with these earlier findings. Among the genes that have significantly different expression patterns post-IR between the two cell types are several that regulate cell cycle. For example, the expression levels of cyclin B1, cyclin G1 and cyclin G2 were increased in AT carriers relative to normal controls at 2 and 6 hours post-IR. Unlike the AT carriers' cells, cells from normal individuals do not activate cyclins after exposure to IR, and therefore, arrest at G1/S and G2/M to permit DNA repair. In contrast, cells from AT carriers proceed to DNA synthesis steps despite the radiation damage. ATM protein is a protein-tyrosine kinase involved in early steps of DNA damage response. Thus, it is perhaps not surprising to find that mutations in one copy of the ATM gene can cause a plethora of changes in the genes downstream of ATM—with many of them involved in regulation of cell proliferation and cell death.

A number of studies emphasize the variability of individual results from microarray studies (Lee et al, 2000; Newton et al, 2001; Tusher et al, 2001). Two approaches which limit the problems that result from technical variability were applied. First, the hybridization experiments were repeated four times, and the most extreme value from each set of reactions was eliminated. This simple statistical procedure reduced the experimental variation and increased the chance of finding differences that are consistent and reliable. Second, in the IR response experiment, pooled RNA from several subjects in each group were used instead of RNA from individuals. This procedure also increased the likelihood of detecting differences that are consistent between the two groups.

Clinically, it is important to develop methods for identifying AT carriers and to understand their radiosensitivity. Previous studies have indicated that ionizing radiation used in diagnosis and treatment may trigger the development of cancer in AT carriers (Swift et al, 1986; Swift et al, 1991; Athma et al, 1996; Broeks et al, 2000). The dose of radiation used in this study was relatively low and comparable to the dose that AT carriers may receive from diagnostic procedures and environmental exposure. Thus the marked differences detected in expression of relevant genes were not the result of unusually high levels of irradiation. This observation reinforces the need to take a more active role in identifying AT carriers, in order to minimize their risk of developing radiation-induced cancers.

EXAMPLE 2

Methods for Identifying Heterozygous Carrier of Autosomal Recessive Disorders

The method described in Example 1 for identifying AT carriers from normal individuals based on altered gene expression patterns may be adapted to identify heterozygous carriers of a variety of other autosomal recessive disorders including, but not limited to Cystic Fibrosis (CF), Sickle Cell Anemia, Tay-Sachs disease, Phenylketonuria (PKU), Oculocutaneous Albinism (OCA), Hereditary Haemochromatosis (HH), AAT deficiency, ADA deficiency, β-thalassemia, alpha-1 antitrypsin deficiency, Spinal Muscular Atrophy, Friedreich's Atoxia, and Congenital Adrenal Hyperplasia.

To identify heterozygous carriers of autosomal recessive disorders, cDNA microarrays may be used to examine the expression profiles of total RNA from lymphoblastoid cell lines of heterozygous carriers for any one of the autosomal recessive disorders which have been previously identified by conventional means and lymphoblastoid cell lines from a pool of normal individuals (those who are selected from a pool of non-heterozygous carriers). Standard linear discriminate analysis can be used to assess the differences in expression profiles between cells from heterozygous carriers and normal individuals. Identification of different gene expression profiles between heterozygous carriers and normal individuals facilitates clinical discrimination between the heterozygous carriers and normal individuals based on this "genetic signature". Accordingly, in this fashion, "genetic signatures" may be obtained for any heterozygous carriers of autosomal recessive diseases. "Genetic signatures" as used herein refers to those subsets of differentially expressed genes present in heterozygous carriers of autosomal recessive disorders when compared to their expression in normal individuals.

REFERENCES

Savitsky, K. et al. A single ataxia telangiectasia gene with a product similar to PI-3 kinase. Science 268, 1749–1753 (1995).

Swift, M., Morrell, D., Cromartie, E., Chamberlin, A. R., Skolnick, M. H. & Bishop, D. T. The incidence and gene frequency of ataxia-telangiectasia in the United States. Am. J. Hum. Genet. 39, 573–583 (1986).

Swift, M., Morrell, D., Massey, R. B. & Chase, C. L. Incidence of cancer in 161 families affected by ataxia-telangiectasia. New England J. Med. 26, 1831–1836 (1991).

Athma, P. et al. Molecular genotyping shows that ataxia telangiectasia heterozygotes are predisposed to breast cancer. Cancer Genet. Cytogenet. 92, 130–134 (1996).

Broeks, A. et al. ATM-heterozygous germline mutations contribute to breast cancer-susceptibility. Am. J. Hum. Genet. 66, 494–500 (2000).

Swift, M. et al. Malignant neoplasms in the families of patients with ataxia telangiectasia. Cancer Res. 36, 209–215 (1976).

Gilad, S. et al. Ataxia-telangiectasia: founder effect among north African Jews. Hum. Mol. Genet. 12, 2033–7 (1996).

Wright, J. et al. A high frequency of distinct ATM gene mutations in ataxia-telangiectasia. Am. J. Hum. Genet. 59, 839–46 (1996).

Concannon, P. & Gatti, R. A. Diversity of ATM gene mutations detected in patients with ataxia-telangiectasia. Hum. Mutations 10, 100–107 (1997).

Telatar, M. et al. Ataxia-Telangiectasia: mutations in ATM cDNA detected by protein truncation screening. Am. J. Hum. Genet. 59, 40–44 (1996).

Weeks, D. E. et al. Assessment of chronic gamma radiosensitivity as an in vitro assay for heterozygote identification of ataxia-telangiectasia. Radia. Res. 128, 90–99 (1991).

Ashburner, M. (The Gene Ontology Consortium) et al. Gene Ontology: tool for the unification of biology. Nat. Genet. 25, 25–29 (2000).

Bach, I. The LIM domain: regulation by association. Mech. Dev. 91, 5–17 (2000).

Efferth, T., Fabry, U. & Osieka, R. DNA damage and apoptosis in mononuclear cells from glucose-6-phosphate dehydrogenase patients after UV irradiation. J. Leukoc. Biol. 69, 340–342 (2001).

Tuttle, S., Stamato, T., Perez, M. L. & Biaglow, J. Glucose-6-phosphate dehydrogenase and the oxidative pentose phosphate cycle protect cells against apoptosis induced by low doses of ionizing radiation. Radiat. Res. 153, 781–787 (2000).

Minutesamoto, S. et al. Cloning and functional analysis of new members of STAT induced STAT inhibitor (SSI) family: SSI-2 and SSI-3. Biochem. Biophys. Res. Comm. 237, 79–83 (1997).

Roberts, D. D. Regulation of tumor growth and metastasis by thrombospondin-1. FASEB J. 10, 1183–1191 (1996).

Heald, R., McLoughlin, M. & McKeon, F. Human WEE1 maintains mitotic timinutesg by protecting the nucleus from cytoplasmically activated Cdc2 Kinase. Cell 74, 463–474 (1993).

Hirai, H. et al. Novel INK4 proteins, p19 and p18 are specific inhibitors of the cyclin D-dependent kinases CDK4 and CDK6. Mol. Cell Biol. 15, 2672–2681 (1995).

Juan, J. et al. Histone deacetylases specifically down-regulate p53-dependent gene activation. J. Biol. Chem. 275, 20436–20443 (2000).

Powis, G. & Montfort, W. R. Properties and biological activities of thioredoxins. Annu. Rev. Biophys. Biomol. Struct. 30, 421–455 (2001).

Powis, G., Mstacich, D. & Coon, A. The role of redox protein thioredoxin in cell growth and cancer. Free Radic. Biol. Med. 29, 312–322 (2000).

Yuan, S. et al. Identification and characterization of human beta-2-chimaerin: association with malignant transformation in astrocytoma. Cancer Res. 55, 3456–3461 (1995).

Pruitt, K. & Der, C. J. Ras and Rho regulation of the cell cycle and oncogenesis. *Cancer Lett.* 171, 1–10 (2001).

McLaughlin, M. M. et al. Identification of mitogen-activated protein (MAP) kinase-activated protein kinase-3, a novel substrate of CSBP p38 MAP kinase. *J. Biol. Chem.* 271, 8488–8492 (1996).

Golub, T. R. et al. Molecular Classification of Cancer: Class Discovery and Class Prediction by Gene Expression Monitoring *Science* 286, 531–537 (1999).

Bittner, M. et al. Molecular classification of cutaneous malignant melanoma by gene expression profiling. *Nature* 406, 536–540 (2000).

Perou, C. M. et al. Molecular portraits of human breast tumors. *Nature* 406, 747–752 (2000).

Alizadeh, A. A. et al. Distinct types of diffuse large B-cell lymphoma identified by gene expression profiling. *Nature* 403, 503–511 (2000).

Paterson, M. C., Anderson, A. K., Smith, B. P. & Smith, P. J. Enhanced radiosensitivity of cultured fibroblasts from ataxia telangiectasia heterozygotes manifested by defective colony-forminutesg ability and reduced DNA repair replication after hypoxic gamma irradiation. *Cancer Res.* 39, 3725–3734 (1979).

West, C. M., Elyan, S. A., Berry, P., Cowan, R. & Scott, D. A comparison of the radiosensitivity of lymphocytes from normal donors, cancer patients, individuals with ataxia telangiectasia and A-T heterozygotes. *Int. J. Radiat. Biol* 68, 197–203 (1995).

Barlow, C., Eckhaus, M. A., Schaffer, A. A. & Wynshaw-Boris, A. Atm haploinsufficiency results in increased sensitivity to sublethal doses of ionizing radiation in mice. *Nature Gen.* 21, 359–360 (1999).

Xu, Y. & Baltimore, D. Dual roles of ATM in the cellular response to radiation and in cell growth control. *Genes Dev.* 10, 2401–10 (1996).

Shigeta, T. et al. Defective control of apoptosis and mitotic spindle checkpoint in heterozygous carriers of ATM mutations. *Cancer Res.* 59, 2602–2607 (1999).

Lee, M. L., Kuo, F. C., Whitmore, G. A. & Sklar, J. Importance of replication in microarray gene expression studies: statistical methods and evidence from repetitive cDNA hybridization. *Proc. Natl. Acad. Sci. USA* 97, 9834–9839 (2000).

Newton, M. A. et al. On differential variability of expression ratios: improving statistical inference about gene expressionchanges from microarray data. *J Comput. Biol.* 8, 37–52 (2001).

Tusher, V. G., Tibshirani, R. & Chu, G. Significance analysis of microarrays applied to the ionizing radiation response. *Proc. Natl. Acad. Sci. USA* 98, 5116–5121 (2001).

Altschul, S. F., Gish, W., Miller, W., Myers, E. W. & Lipman, D. J. Basic local alignment search tool. *J. Mol. Biol.* 215, 403–410 (1990).

Pruitt, K. D. & Maglott, D. R. Refseq and Locuslink: NCBI gene-centered resources. *Nucl. Acids Res.* 29, 137–140 (2001).

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for identifying a genetic signature for heterozygous carriers of autosomal recessive disorders, said carriers not expressing a phenotype associated with said disorder, comprising the steps of:
   a) obtaining a nucleic acid sample from cells of heterozygous carriers and normal individuals;
   b) generating detectably labeled probes from said nucleic acid samples;
   c) contacting cDNA microarrays with said detectably labeled probes under conditions that facilitate hybridization between complementary nucleic acids, if any are present;
   d) analyzing said cDNA microarrays for cDNA hybrids, if any are present; and
   e) comparing hybridization profiles from said heterozygous carrier and normal nucleic acid samples, thereby generating a genetic signature which corresponds to said autosomal recessive disorder, said genetic signature comprising those particular nucleic acid sequences which are differentially expressed between said heterozygous carriers and normal individuals.

2. The method of claim 1, wherein said cells are lymphoblastoid cells.

3. The method of claim 1, wherein said RNA samples are reverse transcribed with Cy3 fluorescent tags into labeled cDNA.

4. The method of claim 1, wherein said cDNA microarray contains at least 3000 cDNA clones.

5. The method, of claim 1 further comprising the steps of:
   f) performing linear discrimination analyses to derive discriminant functions for each reaction; and
   g) assigning individuals as either a heterozygous carrier or normal individual based on said discriminant functions.

6. The method of claim 1, wherein said method is used to identify heterozygous carriers of autosomal recessive disorders selected from the group consisting of Ataxia telangiectasia, Cystic Fibrosis (CF), Sickle Cell Anemia, Tay-Sachs disease, Phenylketonuria (PKU), Oculocutaneous albinism (OCA), Hereditary Haemochromatosis (HH), ATT deficiency, ADD deficiency, beta-thalassemia, alpha-1 antitrypsin deficiency, Spinal Muscular Atrophy, Friedreich's Atoxia, and Congenital Adrenal Hyperplasia.

7. The method of claim 6, wherein said method is used to identify heterozygous carriers of Ataxia telangiectasia.

* * * * *